United States Patent [19]

Danto

[11] Patent Number: 4,672,978
[45] Date of Patent: Jun. 16, 1987

[54] BRAIN STIMULATION OF BALANCE RESPONSE

[76] Inventor: Joseph Danto, 1088 Bromley Ave., Teaneck, N.J. 07666

[21] Appl. No.: 661,908

[22] Filed: Oct. 17, 1984

[51] Int. Cl.⁴ .............................................. A61B 5/10
[52] U.S. Cl. .................................... 128/782; 128/731; 5/67; 5/434; 5/437
[58] Field of Search ................................ 128/731–732, 128/774, 782, 48–50, 376–378; 5/62, 66–68, 431–434, 437

[56] References Cited

U.S. PATENT DOCUMENTS

| | | | |
|---|---|---|---|
| 3,614,950 | 10/1971 | Rabey | 128/774 |
| 3,737,924 | 6/1973 | Davis | 5/62 X |
| 3,748,666 | 7/1973 | Seng | 5/61 |
| 4,062,075 | 12/1977 | Stern et al. | 5/68 X |
| 4,081,867 | 4/1978 | Simeola | 5/433 X |
| 4,441,220 | 4/1984 | Peterson | 128/376 X |

FOREIGN PATENT DOCUMENTS 0736957 6/1980 U.S.S.R. .............................. 128/782
0904666 2/1982 U.S.S.R. .............................. 128/782

OTHER PUBLICATIONS

Gilman et al., "Measurement of Head Movement During Auditory Localization", *Behavior Research Methods and Instrum.*, vol. 11(1), pp. 37–41, 2-1979.

Primary Examiner—Kyle L. Howell
Assistant Examiner—Angela D. Sykes
Attorney, Agent, or Firm—Thomas Langer

[57] ABSTRACT

A technique is disclosed for evoking a brain response of the balance function. The stimulus used for evoking the response is rapid movement of the head through an arc and at a rate of acceleration selected to minimize interference from other, unwanted responses. The brain signals are simultaneously monitored with an electroencephalograph machine and processed to obtain the desired signals.

18 Claims, 2 Drawing Figures

BRAIN STIMULATION OF BALANCE RESPONSE

BACKGROUND OF THE INVENTION

This invention relates to a technique for stimulating brain waves and, in particular, to evoking an electrical brain response corresponding to a person's balance function.

In order to form a diagnosis of possible disease, clear and objective information is required. Often such information is difficult or impossible to obtain due to the nature of the disease or to the inability or unwillingness of the patient to cooperate. The latter is particularly true for difficult-to-test patients such as babies, patients unable to communicate, patients unwilling to reveal the full range of their disability, and patients with inconclusive or inconsistent symptoms. This can be overcome with evoked response testing. It uses a technique which includes exposing the patient to a stimulus and measuring the resultant brain signals generated in response to the stimulus. Evoked response testing can be non-invasive (i.e. no foreign matter is introduced into the body) so that the information is obtainable safely. Also, testing can be repeated as often as necessary in obtaining all the information needed to evaluate the course of the disease and/or treatment.

Measurement techniques exist and are well known for detecting signals generated in the brain. Electro-encephalography is now recognized and well established. Tests have been developed using electro-encephalography to, for example, provide an indication whether a sensory stimulus propagates through the nervous system to the brain, reveal specific brain activity in response to a stimulus, distinguish a normal from an abnormal response, and to determine whether a disorder is psychogenic rather than organic.

In all of these measurements, a primary obstacle in getting usable results is the low signal-to-noise ratio of the detected signal. The signals which are typically detected through the scalp are low in amplitude. Moreover, the brain has continual activity which creates a background noise from which it is difficult to distinguish the evoked signals due to a particular stimulus.

To overcome this problem, a technique known as computer averaging was developed. It is disclosed in U.S. Pat. No. 3,087,487. A unit which implements this technique can be purchased from Nicolet Biomedical Division in Madison, Wis. by specifying Model No. CA-1000. Briefly, the subject is exposed to a series of stimuli which can be, for example, visual, auditory, or tactile. The electrical responses to these stimuli are measured by electrodes attached to appropriate regions of the head and body and processed by a computerized electro-encephalograph machine. The detected signals are correlated with the generated stimuli. Since the background brain activity averages out at a steady level, a summation of the evoked responses to a plurality of such stimuli creates a processed signal readily distinguishable from the background noise.

Aside from the difficulty of distinguishing the brain's evoked response from its background noise, which has now been overcome, no safe technique has been developed to focus on testing the balance function of human beings with an evoked response. Such information is required, for example, to determine whether the balance mechanism in the ear functions properly and whether the neural pathways are intact and operational. The problem is how to stimulate that particular brain response so a signal can be evoked indicative of the state of the subject's balance function. The known auditory, visual and tactile stimuli used to date in evoked response testing do not evoke the desired balance function brain response.

One technique now in use on human beings for lack of any other to accomplish this aim is known as the "bithermal caloric test". It is a test which involves irrigating the outer ear canal with water. However, it causes side effects such as dizziness and nausea. Moreover, it can stimulate the vagus nerve which controls breathing, and in rare cases death can result if the subject's breathing is thereby impaired. Because of the discomfort and danger involved, it is used relatively sparingly in the first place, and only rarely for repeat testing.

Another approach for evoking a balance function brain response has been used on small animals such as mice and cats. It has been reported in the article "Short Latency Vestibular Evoked Response to Acceleration Stimuli Recorded by Skin Electrodes" authored by Elidan, Sohmer, Lev and Gay appearing in Ann Otol Rhinol Laryngol 93:84, and the article "Recording of Short Latency Vestibular Evoked Potentials to Acceleration in Rats by Means of Skin Electrodes" authored by Elidan, Sohmer and Nizan appearing in Electroencephalograph Clin Neurophysical 1982:53:501-15. Their approach requires rotation of the entire animal within a cage. This is not practical, and may even be dangerous, for human beings.

SUMMARY OF THE INVENTION

It is a general object of the invention to test the balance function of a human being.

It is a more specific object of the invention to test the balance function by evoking brain signals.

Another object of the invention is to provide a stimulus for evoking the brain's balance response.

Yet another object of the invention is to evoke the brain's balance response in a convenient, rapid, safe and inexpensive manner.

A further object of the invention is to evoke the brain's balance response to test whether the neurological pathways are intact.

These and other objects of the invention are attained in accordance with one aspect of the invention with a method for evoking brain signals in a human subject related to the balance response function comprising the steps of rotating the subject's head through an arc, completing the rotation through the arc in a test time period selected to minimize undesired responses, returning the head to the start position, repeating the above steps a plurality of times, and monitoring the brain signals as the above steps are performed.

Another aspect of the invention is directed to apparatus for use in evoking brain signal in a human subject related to the balance response comprising a support, a motor secured to the support, means for controlling the motor, a movable cradle to support the subject's head, drive means coupling the cradle to the motor, and means to secure the subject's head to the cradle.

BRIEF DESCRIPTION OF THE DRAWINGS

For a better understanding of the invention, as well as other objects and features thereof, reference is made to the following detailed description to be read in conjunction with the accompanying drawings, which are.

DETAILED DESCRIPTION OF THE DRAWINGS

The invention provides an apparatus to stimulate the brain's balance response by moving the subject's head in a predetermined motion. One aspect of the invention is the discovery that the brain's balance response can be stimulated by rapidly rotating the head around an axis extending from the neck through the top of the head. The motion must be done in such a way so as to stimulate the balance response without appreciably firing the muscle fibers in the neck. Should the neck muscles react, the resulting brain activity would swamp any signals evoked due to the balance function. As discussed below, the desired response can be evoked while avoiding undesired responses by selecting, for example, certain parameters for the arc and frequency of the rotation.

Figure 1:
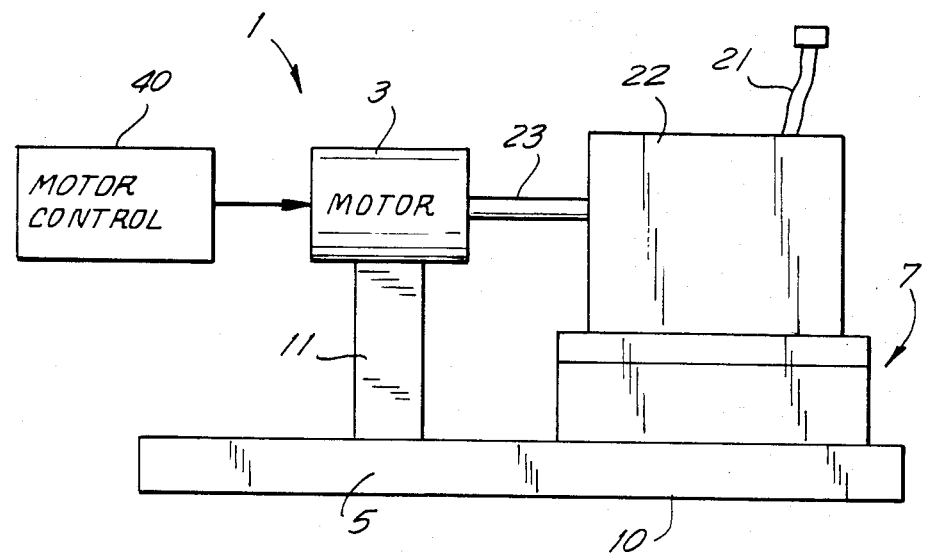
FIG. 1 is a side view of the invention.
Figure 2:
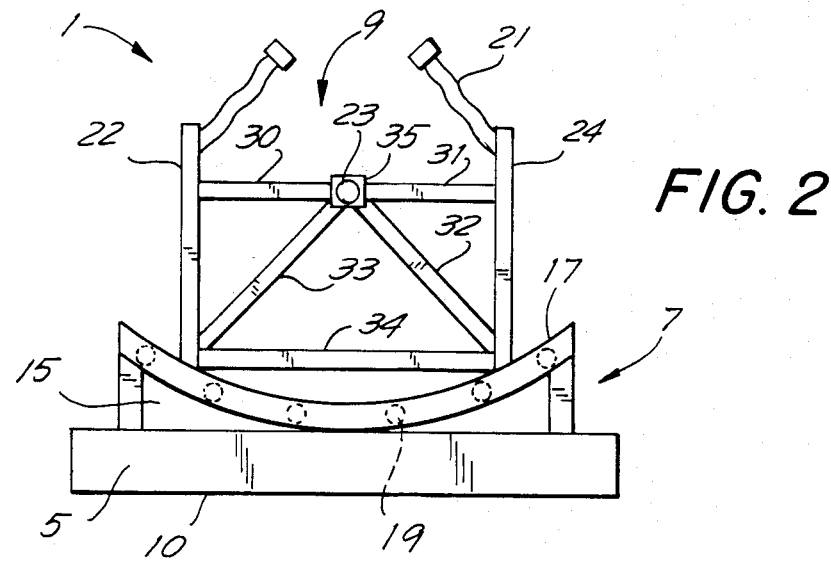
FIG. 2 is a front view of the invention.

To this end, the apparatus 1 as shown in FIGS. 1 and 2 includes the following major elements: a motor 3 fixed to stand 5 which is itself stationary and secured in place to prevent movement during operation. A headrest 7 is provided to support the head of the patient in a horizontal position. Headrest 7 is moveable. Drive means 9 couples motor 3 to headrest 7 so that the patient's head is moved in a desired fashion as motor 3 is actuated.

Turning now more specifically to FIG. 1, apparatus 1 includes stand 5 which has a flat bottom surface 10 so it can rest on a stable, stationary platform (not shown) such as a bed or table. Stand 5 is anchored, as by clamps (not shown), to such platform so that it will not move during operation of motor 3 as, for example, due to motor vibration or movement of the patient. Bar 11 extends upward from stand 5 and is secured to the housing of motor 3. This can be done in any one of a variety of well known ways such as welding, with fasteners such as screws, or with clamps. Cost and sturdiness will determine which of these alternatives is selected. Motor 3 is, of course, connected to an activation switch (not shown) and a power source (not shown). This motor must be of a type powerful enough to move the subject's head a short distance at a rapid rate and great acceleration, for reasons discussed below. An example of such a motor is TURN-ACT 1 available from the Turn-Act Co. in Jefferstown, Ky.

Headrest 7, as seen in both FIG. 1 and FIG. 2, is preferably shaped in an arc and may be suitably padded for the comfort of the subject. The headrest includes base 15 secured to stand 5 and a moveable cradle portion 17. Headrest 7 is horizontal and is long enough to receive the patient's head from approximately the neck up. The arcuate shape of headrest 7 is preferred in order to have it somewhat contoured to the shape of the back of the head. This results in a distribution of weight over a wider area and prevents or at least minimizes patient discomfort. Ball bearings 19 lie between base 15 and cradle portion 17 to provide for relatively friction free rotation of cradle 17. Head retainers 22 and 24 extend vertically from cradle 17. Retainers 22 and 24 are attached to cradle 17 in any one of several well known ways, and details are not deemed necessary. The patient's head fits between these retainers which thus prevent it from any significant lateral movement on the cradle 17. A strap 21 is used in a well known to aid in holding the subject's head down on cradle 17. It is strapped to the patient's forehead so the head cannot be raised off cradle 17.

Drive means 9 includes an arrangement of brackets 30–33 affixed to pin 35. Pin 35 has a hole in it with one flat side which accomodates motor shaft 23 having a corresponding flat to transmit rotation of the shaft to cradle 17. Brackets 30 and 31, along with a bracket 34 are horizontal and help to stiffen the structure by keeping retainers 22 and 24 in piece. Brackets 32 and 33 are slanted and extend from pin 35 to an end of bracket 34. These are also used for stability of the structure.

Motor control means 40 is provided to set the parameters, discussed below, for the movement of the subject'head, such as the arc, test time period, period for return to the start position, and the number of repetitions. Such a control is well known and forms no part, in and of itself, of this invention. Thus, no details are deemed necessary.

It has been discovered in accordance with one aspect of the invention that the desired brain response of the balance function can be evoked without simultaneously evoking interfering responses by rotating the head through an arc of approximately 5° to 8° during a period of 1–1.5 seconds. This arc and rate of acceleration provide the required brain response of the balance function yet are such that, for example, the neck muscles do not stiffen. A repetition of 250 such movements is preferred to produce a good reading with the above-mentioned computer averaging technique. The above-mentioned motor has been selected for its ability to generate the short bursts of power required in designated fractions of a revolution.

As the subject's head is rotated, say from right to left, the motion will stimulate, or evoke, a brain response indicative of the balance function from the left ear while inhibiting such a reaction in the right ear. Therefore, in the preferred technique, the response from each ear is tested separately in order to simplify the equipment required. The left ear is, thus, tested by rotating the head through the above-mentioned arc in the span of 1–1.5 sec. only from right to left. The head is then returned to the start position in a considerably longer time period. This period should not be overly long since it will then unduly lengthen the time required to complete the test. A period of approximately one half second has been found satisfactory. To test the brain response due to the right ear, the rotation is reversed. Thus, the head will be rotated from left to right within 1–1.5 m sec while it will return from right to left in approximately one half second.

As has already been mentioned, the position of the subject's head is horizontal and he is preferably supine. In this position, the patient's head will be rotated about an axis extending from the neck to the top of the head. Only the lateral (horizontal) semicircular canal will be thereby stimulated to evoke a balance response. With the bithermal caloric technique mentioned above, only this canal was testable for reasons of convenient access since it is the closest to the exterior of the ear. Two other canals exist, however, toward the middle of the ear and can be tested with the invention. This can be accomplished by changing the axis about which the head is oscillated. One such axis extends through the ears and another extends from the nose to the back of the head. Apparatus similar to that shown in the drawings can be used for such a purpose.

In operation, the probes are placed on the subject's scalp and are connected to the electro-encephalograph.

The subject's head is then placed horizontally in and affixed to headrest 7. Motor 3 is activated for a number of movements preset in motor control means 40 while measurements of brain activity are being taken. The brain signals are processed by inputting them along with timing signals synchronized with the rotation of the head to a computer averaging apparatus, such as disclosed in the above-mentioned U.S. Pat. No. 3,027,487 and available from Nicolet. The resulting processed signal is representative of the brain's balance response. This signal can then be used for the evaluation of vestibular function and clinical assessment of physiologic integrity.

It should be understood that the above desription depicts in detail the preferred embodiment and the best mode of the invention. However, it should be readily apparent that a number of modifications to the disclosed apparatus can readily be made. For example, the support for the headrest can be varied. Also, the retainers 22 and 24 can be made adjustable to accomodate heads of various sizes, such as those of an adult vs. that of a child. The selected parameters for arc, test time period, return-to-start position time period and the number of test movements can also be varied. For example, an arc with range of 1°–20°, a test time period of 1–5 m sec, a return-to-start time period of 1 sec, and 10–500 test movements could be used. Also, the test can be administered in moving the head from one side to the other, and then back again, rather than doing it in two stages as described above. Additional electronics would be required to interpret the resulting brain signals. These and other modifications are included in the scope of the invention as defined by the following claims:

I claim:

1. An apparatus for stimulating brain signals representative of a human subject's balance function, comprising:
   means for supporting a human subject;
   a moveable headrest adapted to be placed on said means for supporting, said headrest adapted to accommodate and support only the head of said subject;
   means coupled to said headrest for causing it to move relative to the said means for supporting through an arc for a predetermined plural number of cycles to move said head relative to the body of said subject.

2. The appartus of claim 1 wherein the said movement is rotational so as to rotate the subject's head from side to side about an axis running from the neck through the top of the head.

3. The apparatus of claim 2 wheren the arc of rotation is between 1° and 20°.

4. The apparatus of claim 3 wherein the number of cycles is in the range of 100–500.

5. The apparatus of claim 4 wherein the time period for completing the motion through said arc is in the range of 1–5 m sec.

6. The apparatus of claim 4, wherein only the head is moved by said means coupled to the headrest.

7. A method for evoking brain signals in a human subject related to the balance response function comprising the steps of:
   (a) rotating the head of said subject relative to the body of said subject from a start position through an arc;
   (b) completing the rotation through said arc in a test time period selected to minimize undesired brain signal response;
   (c) returning the head to the start position; and
   (d) repeating the above steps a selected plurality of times.

8. The method of claim 7, wherein the axis of said arc extends from the subject's neck through the top of said head.

9. The method of claim 7, wherein the axis of said arc extends through the subject's ears.

10. The method of claim 9, wherein the axis of said arc extends from the subject's nose to the back of said head.

11. The method of claim 7, wherein said arc is in the range of 1°–20°.

12. The method of claim 11, wherein said arc is in the range of 5°–8°.

13. The method of claim 7, wherein said test time period is in the range of 1–5 m sec.

14. The method of claim 13, wherein said test time period is in the range of 1–1.5 m sec.

15. The method of claim 7, wherein steps a, b, and c are repeated from 10–500 times.

16. The method of claim 15, wherein the number of times steps a, b, and c are repeated is 250.

17. The method of claim 7, wherein only the head is rotated.

18. Apparatus for use in evoking brain signals in a human subject related to the balance response comprising:
   a support;
   a motor secured to said support;
   means for controlling said motor;
   a movable cradle to support only the subject's head;
   drive means coupling the cradle to the motor; and
   means to secure the subject's head to the cradle.

* * * * *